United States Patent [19]

Leuchtenberger

[11] Patent Number: 4,742,820
[45] Date of Patent: May 10, 1988

[54] DEVICE FOR INTRODUCING A DIAPHRAGM

[76] Inventor: Hannegret Leuchtenberger, Schillerpromenade 32 33, 1000 Berlin 44, Fed. Rep. of Germany

[21] Appl. No.: 879,122

[22] PCT Filed: Sep. 17, 1985

[86] PCT No.: PCT/DE85/00327
§ 371 Date: May 20, 1986
§ 102(e) Date: May 20, 1986

[87] PCT Pub. No.: WO86/01708
PCT Pub. Date: Mar. 27, 1986

[51] Int. Cl.$^4$ ............................................. A61F 5/46
[52] U.S. Cl. ........................................ 128/127; 604/55
[58] Field of Search ........................... 128/127-131; 604/55, 285, 11-17

[56] References Cited

U.S. PATENT DOCUMENTS

| | | | |
|---|---|---|---|
| 2,141,040 | 12/1938 | Holt | 128/127 |
| 3,918,452 | 11/1975 | Cornfeld | 604/11 X |
| 4,398,532 | 8/1983 | Sweeney, III | 128/127 |
| 4,428,370 | 1/1984 | Keely | 128/127 |
| 4,543,086 | 9/1985 | Johnson | 604/15 |

FOREIGN PATENT DOCUMENTS 0530318 12/1940 United Kingdom ............... 604/15

*Primary Examiner*—Richard J. Johnson
*Attorney, Agent, or Firm*—Basile and Hanlon

[57] ABSTRACT

A device for introducing a diaphragm into a vagina as well as for placing it in front of the womb, essentially consisting of an insertion rod to which the diaphragm can be attached in a detachable manner, whereby the insertion rod is designed to be hollow and at its end opposed to the insertion end a piston-shaped insert is provided, which can be moved in relation to the insertion rod.

5 Claims, 2 Drawing Sheets

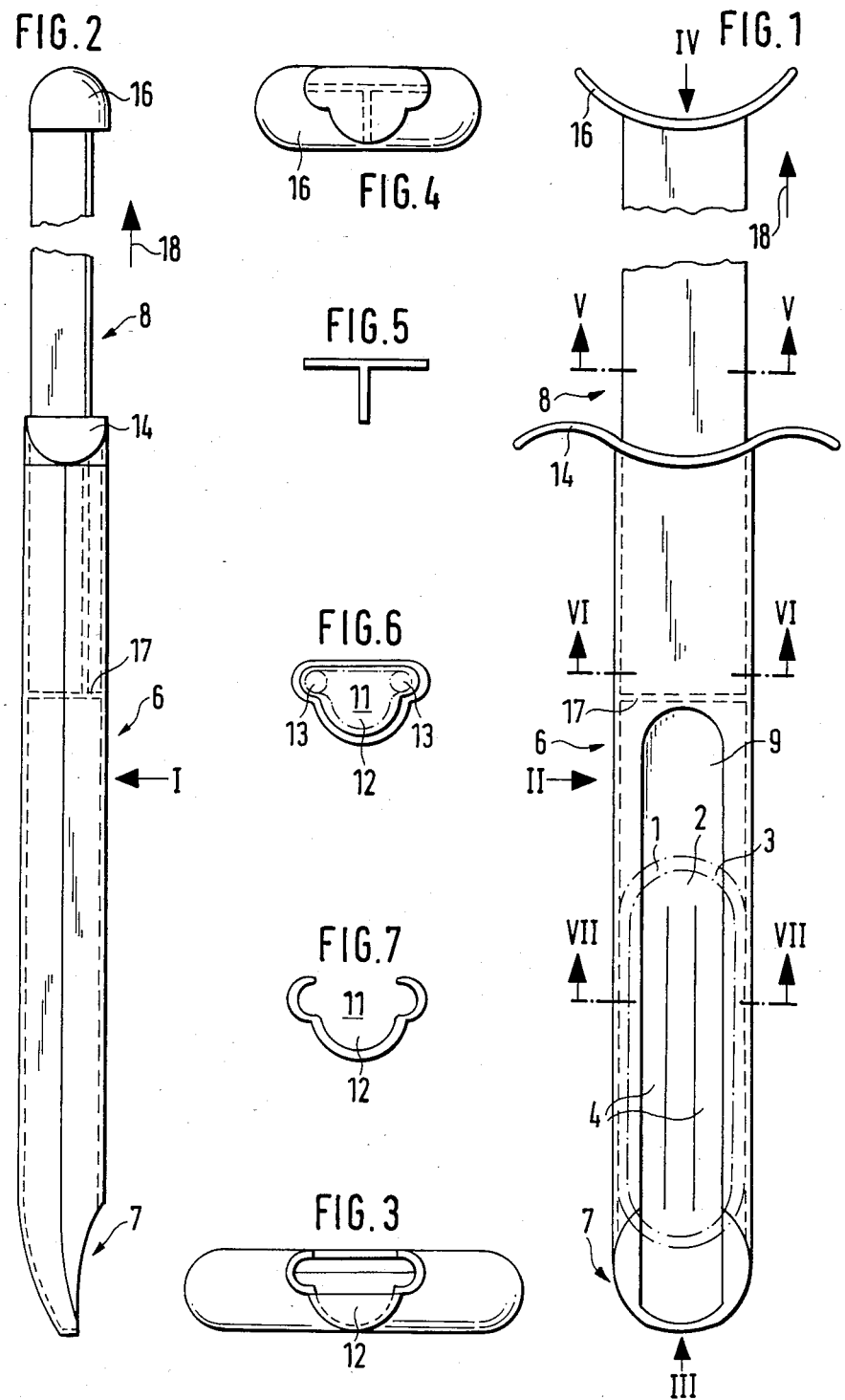

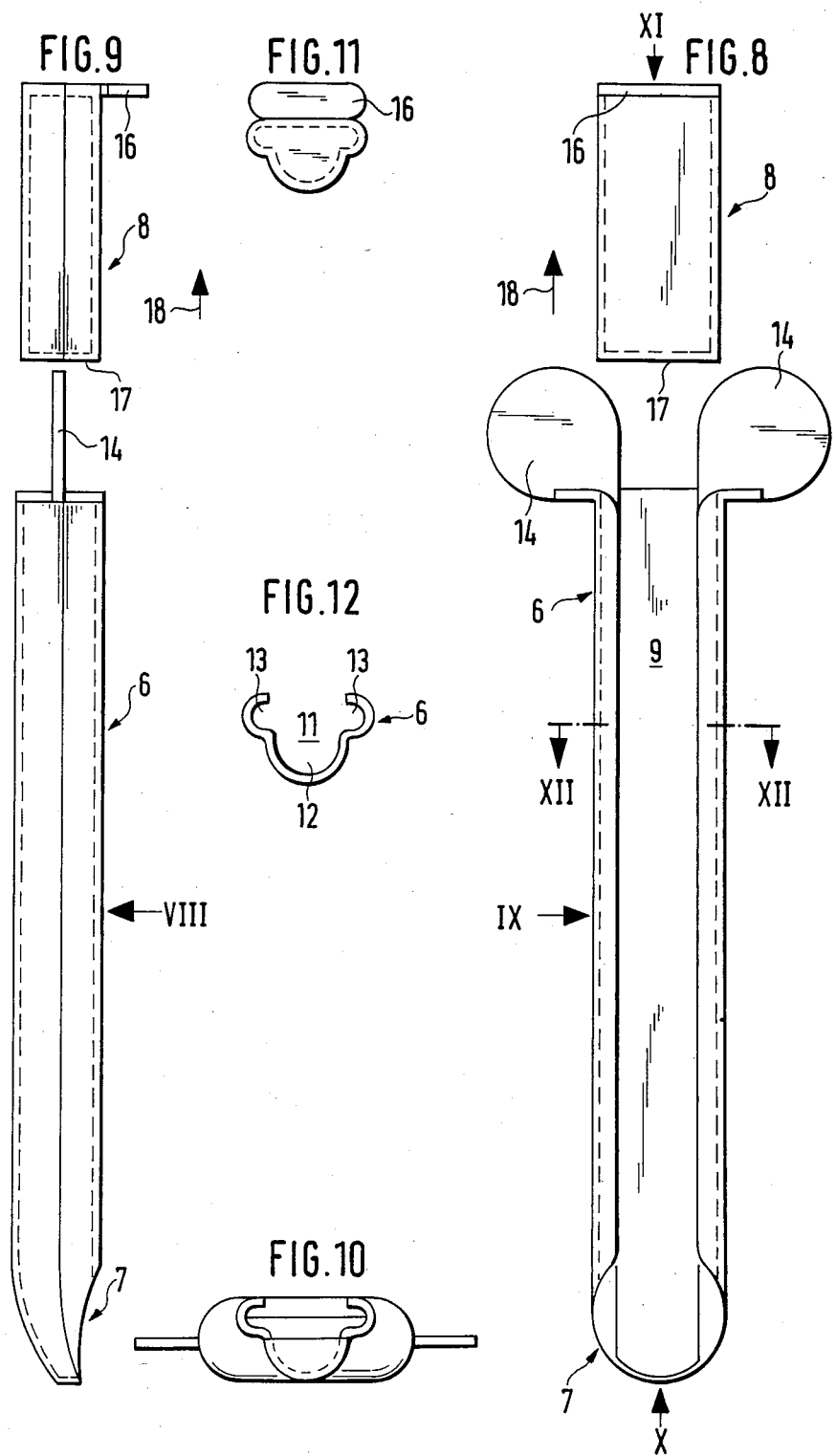

DEVICE FOR INTRODUCING A DIAPHRAGM

BACKGROUND OF THE INVENTION

1. Field of the Invention

The invention relates to a device for introducing a diaphragm into a vagina, as well as for placing it in front of the womb. More particularly, the invention relates to a device having a hollow insertion rod with a longitudinally slotted, open insertion end to which a diaphragm can be detachably fixed which is arranged in a piston displaceable relative to the insertion rod.

2. Description of the Prior Art

As is known, a diaphragm constitutes a contraceptive means, which is inserted in the vagina and positioned in such a way that it seals it off from the womb. As a result the male spermatozoa cannot enter the oviduct, so that fertilization cannot take place. In addition to this mechanical protection, a spermicidal cream, foam or gel is used, which renders the male spermatozoa infertile within a very short time. The conventional diaphragm, in both the stocked state and in the fitted state, is circular and geometrically spherically segmental in plan view and comprises an elastic membrane reinforced in bead-like manner on the edge portion. For insertion purposes, the diaphragm is deformed by lateral compression of the bead at two facing points. This automatically forms two pockets. The automatically formed pockets (and optionally the bead-like edge) then are filled or coated with spermicidal agent such as spermicidal cream or the like.

Although this contraceptive device and method has been known for many years, it has not been as widely used as might have been expected. This is particularly due to the fact that difficulties are encountered in inserting a diaphragm unless aids are used. Furthermore, the coating or partial filling with spermicidal cream or the like leads to both the fingers and the vagina becoming smeared with the spermicidal agent, which is considered to be unpleasant and/or disturbing.

To facilitate the introduction of a diaphragm, an insertion rod has been developed and is known, which is provided at its one end with a slight notch onto which a diaphragm can be fixed prior to introduction and placement in the vagina. For the purpose of this fixing, several additional notches are provided in the central region of the known insertion rod to accommodate different diaphragm sizes. The opposite portion of the bead-like edge can be fixed to one of these notches in the central region of the insertion rod in such a way as was described hereinbefore in connection with manual insertion. In the case of the conventional insertion rod, the diaphragm is taken into the hand in such a way that its curvature points outward and is laterally compressed in the aforementioned manner. Following fixing at the insertion end and in the central portion of the insertion rod, the two aforementioned pockets described in conjunction with manual insertion are formed and filled with the spermicidal agent. It is also recommended that the bead-like edge be coated with cream or the like, in order to improve slidability during insertion.

For insertion and positioning the diaphragm, the insertion rod with the fixed and correspondingly prepared diaphragm is inserted and moved tightly along the lower vagina base up to and behind the opening and is then turned to the side to detach the diaphragm from the insertion rod. This permits the insertion rod to be removed from the vagina. The front edge of the diaphragm is then forced upwards with a finger in such a way that it is positioned behind the pubic bone, where its location is such that it completely covers the opening.

It is readily apparent that, with the conventional insertion rod as the insertion aid, the reservations against this extremely reliable and acceptable contraceptive means cannot be eliminated because the complete handling procedure is still very complicated and because large numbers of potential users object to it. Furthermore, even during the use of this insertion rod, it is not possible to prevent a considerable portion of the spermicidal agent from reaching points where it is not necessary and considered unpleasant and disturbing.

In order to facilitate introduction, U.S. Pat. No. 2,008,380 discloses a device in which the insertion end of the insertion rod is constructed as a head, which is considerably thickened compared with the remaining insertion rod portion. The head is roughly of the same length as the radius of a flexible diaphragm, so that one-half of the diaphragm can be compressed and can be inserted in the insertion head, the other half of the diaphragm projects from the device in an only partially deformed state compared with its normal shape. Even under favorable insertion conditions, a precise positioning of the diaphragm in front of the womb is extremely difficult. Because the diaphragm is flexible, in the case of this conventional device, it can be easily bent sideways during insertion. Under unfavorable circumstances the diaphragm may not even be inserted in the vagina.

In addition, using this device, the spermicidal agent with which the diaphragm is provided comes into contact with the walls of the vagina during insertion, so that part of the spermicidal agent is transferred to the vagina walls. In this known device there is a functionless slot on its underside, which can lead to irritation or even to injuries to the vaginal tissue during insertion.

U.S. Pat. No. 2,141,040 discloses a diaphragm insertion device comprising a cylindrical insertion rod and a cross-sectionally cylindrical piston. This is difficult and unpleasant to insert because the diaphragm must be provided with the spermicidal agent prior to reception in the device, so that said agent necessarily also gets on to the user's fingers. This device is not only anatomically unfavorable, but also unreliable because the user cannot detect from the outside in which relative rotation position with respect to the longitudinal axis she must insert the insertion rod.

U.S. Pat. No. 4,398,532 discloses a diaphragm insertion device with a hollow insertion rod and a piston. The insertion rod has a relatively flat construction and contains both the diaphragm and spermicidal agent. The insertion end of the rod is initially closed by a cap. This known device is intended only for a single use, which, in view of the considerable costs of a diaphragm, is unacceptable for widespread use.

Finally, West German Application No. 17 66 697 discloses a diaphragm insertion device, in which the insertion end portion of a hollow insertion rod contains a multiply folded or rolled up diaphragm which, after expulsion, opens out in such a way that it is correctly positioned in front of the womb. Here again, the diaphragm must initially be provided with spermicidal agent permitting an increased amount of the spermicidal agent to be transferred to the user's fingers, because the diaphragm is not only laterally compressed, but is also deformed. This orientation is also disadvantageous in connection with a correct positioning in front of the womb.

Thus, it is desirable to so improve the known diaphragm insertion devices while avoiding their disadvantages so that insertion can take place effortlessly and without difficulty, even when used for the first time by a relatively unskilled or inexpert user. It is also desirable to provide a diaphragm insertion device in which the diaphragm is inserted in such a way that the diaphragm is correctly positioned in front of the womb while simultaneously ensuring that those vaginal areas where no spermicidal agent is required, as well as a user's fingers do not come into contact with the agent. In addition, the device must be reusable a random number of times and, therefore, easy to clean.

SUMMARY OF THE INVENTION

According to the invention, there is disclosed a diaphragm insertion device in which the internal cross-section of the insertion rod has a cap-like construction through a rounded base and a widened rounded edge region connected thereto for the guided holding of the diaphragm bead. The insertion rod is provided with a single slot arranged in the widened rounded edge region. To supply the diaphragm with a spermicidal agent, the agent can be fed, e.g. from a tube, into the recess-like widened edge regions, which are used for receiving the diaphragm thickened bead-like portion of the diaphragm before the diaphragm is inserted in a laterally compressed state through the open insertion end into the hollow insertion rod. Thus, e.g. strip-like regions of the diaphragm area accessible through the slot can be provided with spermicidal agent. Due to the cap-shaped cross-sectional design of the present invention, the diaphragm cannot pass upwards out of the slot while in this laterally compressed state. Instead it extends with its folds downward into the base region, so that, during insertion, the spermicidal agent does not smear on to the vagina walls. Only after the complete insertion of the insertion rod into the vagina is the rod retracted relative to the piston-like insert, so that the diaphragm can be correctly positioned with respect to the womb.

Although it is fundamentally sufficient for the slot to merely extend over a length corresponding approximately to the diaphragm length in its laterally compressed state, according to a preferred construction the slot extends over the entire length of the insertion rod. Such a construction has the further advantage that the piston can be made relatively short thus ensuring that the diaphragm is not ejected from the insertion rod by means of the piston prematurely. Instead, following the complete introduction of the insertion rod into the vagina, the piston is held with a finger and the insertion rod can be retracted relative to the piston. This action frees the diaphragm from the insertion rod cavity and position it in front of the womb. Another advantage of this construction is that following use, the insertion rod can be cleaned simply and effectively by a brush or the like adapted to the rod's cross-sectional profile.

It has proved to be particularly appropriate to widen the slot towards the insertion end. Such a widening, which need not necessarily be linked with a cross-sectional enlargement of the insertion rod, facilitates the introduction of the laterally compressed diaphragm into the insertion rod and its ejection from the latter.

It has also proved appropriate for an optimum, automatic positioning at the correct point, while simultaneously taking account of anatomical conditions, for the insertion end of the insertion rod to be slightly curved, as will be explained in greater detail relative to embodiments hereinafter.

DESCRIPTION OF THE DRAWING

The invention is described in greater detail hereinafter relative to non-limitative embodiments and the following attached drawings in which like reference numerals are used to refer to like elements throughout the several drawing figures:

FIG. 1 is a lateral plan view of an inventive device in exploded form, i.e. with a piston drawn out of the hollow insertion rod in the direction of Arrow I in FIG. 2.

FIG. 2 is a lateral plan view of the device according to FIG. 1 in the direction of Arrow II therein.

FIG. 3 is an end or frontal plan view from the insertion end on to the device according to FIGS. 1 and 2 in the direction of Arrow III in FIG. 1.

FIG. 4 is an end or frontal plan view of the device according to FIGS. 1 to 3 in the direction of Arrow IV in FIG. 1.

FIG. 5 is a section through the piston-like insert in the direction of section line V—V (while omitting the handle positioned at the upper end of the piston).

FIG. 6 is a section through the insertion rod (without piston and while omitting the insertion rod handle) in the direction of section line VI—VI.

FIG. 7 is a representation corresponding to FIG. 6 in the direction of section line VII—VII.

FIG. 8 is a variant of a view according to FIG. 1 in the direction of Arrow VIII in FIG. 9.

FIG. 9 is a lateral plan view of the device according to FIG. 8 in the direction of Arrow IX therein.

FIG. 10 is an end or frontal plan view of the device according to FIGS. 8 and 9 from the insertion end in the direction of Arrow X.

FIG. 11 is an end or front plan view of the device according to FIGS. 8 to 10 in the direction of Arrow XI in FIG. 8.

FIG. 12 is a section through the insert in the direction of section line XII—XII.

DESCRIPTION OF THE PREFERRED EMBODIMENT

FIGS. 1 to 7 show relative to an embodiment, a first embodiment of a device for inserting and positioning a diaphragm 1, indicated by a dot-dash lines in FIG. 1, which is circular in plan view in both the stocked and use states and comprises an elastic membrane 2. The edge of the elastic membrane 2 is reinforced by means of an all-round bead 3. In a laterally compressed state, as shown in FIG. 1 and as explained hereinafter, two pockets 4 are automatically formed.

In this embodiment, the device comprises a hollow insertion rod 6 open at its two ends. The hollow insertion rod 6 has an insertion end 7 and a piston 8 opposite thereto. The piston 8 is displaceable relative to rod 6, as will be explained hereinafter.

The jacket of the insertion rod 6 is provided with a through-slot 9 in the end portion having insertion end 7 in the longitudinal direction of the insertion rod 6 and which is widened towards insertion end 7, the latter being curved on the side opposite to through-slot 9, as can in particular be seen in FIG. 2.

The internal cross-section II of insertion rod 6 is cap-shaped, as can in particular be seen in FIGS. 3, 4, 6 and 7. As can be seen in these figures, the insertion rod 6 includes an outwardly curved base region 12 and two opposed side members 13, 13' integrally attached to the curved base region 12. The opposed side members 13, 13' are also outwardly curved and integrally formed with the base region 12. The side members 13, 13' are adapted to guidingly hold a portion of the diaphragm reinforcing bead 3. The base region 12 is generally positioned opposite the through slot 9.

At the end remote from insertion end 7, the insertion rod 6 is provided with a handle 14 constructed in such a way that, upon drawing out the insertion rod 6 against piston 8, the index and middle finger can act on handle 14, while the ball of the thumb can be supported on a handle 16 of the piston-like insert 8.

In the embodiment shown in FIGS. 1 to 7, piston 8 is initially T-shaped (cf. FIG. 5) within its handle 16 and terminates with an end face 17, whose contour corresponds to the internal cross-section 11 of insertion rod 6.

The device according to FIGS. 1 to 7 operates and functions as follows. In the manner shown by dot-dash lines in FIG. 1, a diaphragm 1 in a laterally compressed manner is introduced from the insertion end 7 into the cavity of the insertion rod 6. The bead-like edge 3 of diaphragm 1 is guided in the side members 13 of insertion rod 6. The pockets 4 formed when the diaphragm 1 is compressed extend into the base region 12 of cross-section 11, as indicated by dot-dash lines in FIG. 6. Once in position, the diaphragm 1 can be coated with a spermicidal agent from a tube or the like, without the user coming into contact with said agent. During this preparation, the piston 8 is retracted to such an extend that diaphragm 1 can be inserted in the described manner into the insertion rod 6 (cf. FIGS. 1 and 2).

The device with the diaphragm 1 contained therein can then be inserted into the vagina with the through-slot 9 being at the top. Insertion is facilitated by the curvature of the insertion rod 6 at insertion end 7 (cf. FIG. 2). Preferably, the longitudinal portion 20 of the rod 6 opposite the through bore 9 extends beyond the portion 22 immediately adjacent the bore 9 thereby forming an opening angularly oriented to the transverse axis of the rod 6. The portion 20 of the rod 6 which extends beyond the portion 22 immediately adjacent the through bore 9 is, preferably, curved toward the upper portion 22 such that the outermost edge is oriented at essentially the central axis of the rod 6. Following complete insertion of insertion rod 6 in the vagina, the insertion rod 6 is retracted against piston 8 in the direction of Arrow 18. Upon retraction, the end face 17 of piston 8 facing insertion end 7 approaches diaphragm 1 and forces it out of the insertion rod 6. Since the diaphragm 1 is correctly positioned, it is necessarily correctly located in front of the womb with no need for further manipulations being needed. After leaving the insertion rod 6, the diaphragm 1 automatically opens out into its original shape due to the elasticity of bead 3.

It is clear that the spermicidal agent only acts where it is required and that there is no dirtying of the surrounding areas. The device can be reused a random number of times following corresponding cleaning.

FIGS. 8 to 12 show a second embodiment of the present invention in which identical or identically acting parts are given the same reference numerals as in the case of the first embodiment of FIGS. 1 to 7. In this embodiment, the through-slot 9 extends over the entire length of insertion rod 6. This permits the piston 8 to have a randomly short construction because, on removing the insertion rod 6, it only has to be held with one finger relative to said rod 6 and said finger can readily extend into the through-slot 9.

In this second embodiment, the handle 14 of insertion rod 6 is constructed in the manner of two ears, which further aids correct handling. Following the insertion of the insertion rod 6, the rod 6 is removed relative to the fixed insert 8 and not conversely the forward moving towards insertion end 7 of piston 8 relative to the still fixably inserted insertion rod 6.

Apart from the aforementioned and further advantages, it is also pointed out that the construction according to FIGS. 8 to 12 can be easily cleaned and is particularly easy to clean by means of a cleaning body, such as a brush or the like adapted to the internal cross-section 11 of insertion rod 6.

I claim:

1. Device for the insertion of a diaphragm having an elastic membrane and an annular reinforcing bead into a vagina, as well as for the positioning of the diaphragm in front of the womb comprising a hollow insertion rod having a longitudinally slotted open insertion end into which the entire diaphragm can be removably received and a piston extending within the hollow insertion rod and displaceable relative thereto wherein the insertion rod is provided with a single slot terminating in a widened end region and the insertion rod includes:
   (a) an outwardly curved base portion running longitudinally along the insertion rod and located opposite the longitudinal slot; and
   (b) opposed side members defining a widened edge region, each side member having a first edge integrally attached to the curved base portion and a second edge in opposed relation to the second edge on the opposed side member and defining the longitudinal slot, the side members being outwardly curved, the opposed side members adapted to guidingly hold a portion of the diaphragm reinforcing bead.

2. The device according to claim 1 wherein the single slot extends over the entire length of insertion rod.

3. The device according to claim 1 wherein the slot is permanently widened towards the insertion end of insertion rod.

4. The device according to claim 1, wherein the insertion end of insertion rod is curved.

5. The device according to claim 1, wherein the piston has a cross-sectional shape which corresponds to the internal cross-sectional shape of insertion rod.

* * * * *